United States Patent [19]
Deraedt et al.

[11] 4,303,654
[45] Dec. 1, 1981

[54] NOVEL 21-CHLORO-20-ACETYLENIC STEROIDS

[75] Inventors: Roger Deraedt, Pavillons-sous-Bois; Jean G. Teutsch, Pantin; Germain Costerousse, Saint-Maurice, all of France

[73] Assignee: Roussel Uclaf, Paris, France

[21] Appl. No.: 195,647

[22] Filed: Oct. 9, 1980

[30] Foreign Application Priority Data

Oct. 26, 1979 [FR] France ................... 79 26625

[51] Int. Cl.³ .................. A01N 45/00; A61K 31/56
[52] U.S. Cl. ...................... 424/243; 260/239.55 C; 260/397.45; 260/397.5
[58] Field of Search ................ 424/240, 243; 260/397.45

[56] References Cited
U.S. PATENT DOCUMENTS
4,232,015 11/1980 Teutsch et al. ............ 260/239.55 R OTHER PUBLICATIONS
Fried et al., "JACS" vol. 83 (1961) pp. 4663-4664.

Primary Examiner—Elbert L. Roberts
Attorney, Agent, or Firm—Hammond & Littell, Weissenberger and Muserlian

[57] ABSTRACT

Novel 21-chloro-20-acetylenic steroids of the formula

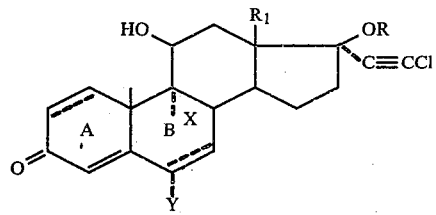

wherein $R_1$ is alkyl of 1 to 3 carbon atoms, R is selected from the group consisting of hydrogen and acyl of an organic carboxylic acid of 1 to 18 carbon atoms, X is selected from the group consisting of hydrogen, chlorine, bromine and fluorine, Y is selected from the group consisting of hydrogen, fluorine and methyl and the dotted lines in the A and B rings are one or two optional double bonds in the 1(2) and 6(7) positions with the proviso that Y is not hydrogen when $R_1$ is methyl, X is hydrogen, the A ring is saturated in the 1(2) position and the B ring is saturated having a remarkable anti-inflammatory activity and their preparation.

24 Claims, No Drawings

NOVEL 21-CHLORO-20-ACETYLENIC STEROIDS

STATE OF THE ART

Related compounds are described in British Pat. No. 919,565 and U.S. Pat. Nos. 3,498,975 and 4,168,306 and commonly assigned U.S. patent application Ser. No. 52,489 filed June 27, 1979 and Ser. No. 63,939 filed July 30, 1979.

OBJECTS OF THE INVENTION

It is an object of the invention to provide the novel 21-chloro-20-acetylenic steroids of formula I and a novel process for their preparation.

It is another object of the invention to provide novel anti-inflammatory compositions and to provide a novel method of treating inflammation in warm-blooded animals.

These and other objects and advantages of the invention will become obvious from the following detailed description.

THE INVENTION

The novel compounds of the invention are 21-chloro-20-acetylenic steroids of the formula

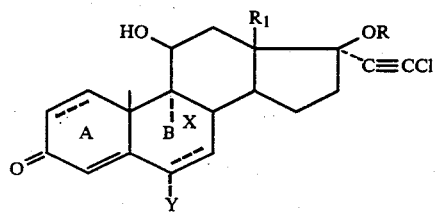

wherein $R_1$ is alkyl of 1 to 3 carbon atoms, R is selected from the group consisting of hydrogen and acyl of an organic carboxylic acid of 1 to 18 carbon atoms, X is selected from the group consisting of hydrogen, chlorine, bromine and fluorine, Y is selected from the group consisting of hydrogen, fluorine and methyl and the dotted lines in the A and B rings are one or two optional double bonds in the 1(2) and 6(7) positions with the proviso that Y is not hydrogen when $R_1$ is methyl, X is hydrogen, the A ring is saturated in the 1(2) position and the B ring is saturated. $R_1$ is preferably methyl or ethyl.

Examples of carboxylic acids of 1 to 18 carbon atoms for the acyl of R are saturated and unsaturated aliphatic and cycloaliphatic carboxylic acids, especially alkanoic acids such as formic acid, acetic acid, propionic acid, butyric acid, isobutyric acid, valeric acid or undecylic acid, hydroxy alkanoic acids such as hydroxylacetic acid, cycloalkyl carboxylic and cycloalkylalkanoic acids such as cyclopropylcarboxylic acid, cyclopentylcarboxylic acid or cyclohexylcarboxylic acid, cyclopentylacetic acid, cyclohexylacetic acid, cyclopentylpropionic acid or cyclohexylpropionic acid; benzoic acid; phenylalkanoic acids such as phenylacetic acid or phenylpropionic acid; and amino acids such as diethylaminoacetic acid or aspartic acid.

Among the preferred compounds of formula I are those wherein $R_1$ is methyl, those wherein X is hydrogen, those wherein the A ring has a double bond in the 1(2) position, those wherein R is hydrogen. Particularly preferred are the compounds of formula I wherein R is hydrogen, $R_1$ is methyl, X is hydrogen and the A ring has a 1(2) double bond.

The process of the invention for the preparation of compounds of formula I comprises reacting a compound selected from the group consisting of the formula

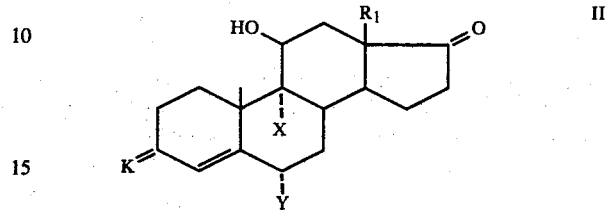

wherein K is ketone blocked as a ketal or oxime,

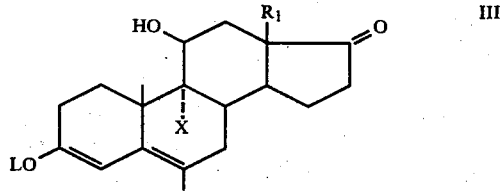

wherein L is alkyl of 1 to 12 carbon atoms and

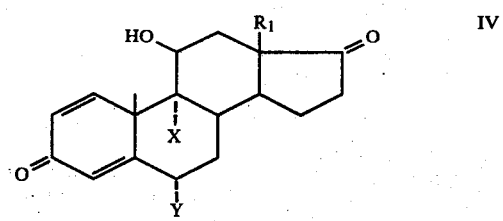

wherein X, Y and $R_1$ have the above definitions with a compound of the formula $$T-C\equiv CCl \qquad V$$

wherein T is selected from the group consisting of lithium, potassium and Hal-Mg- and Hal is a halogen to form, respectively, a compound selected from the group consisting of

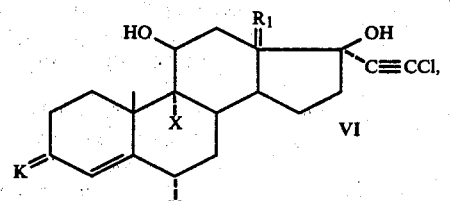

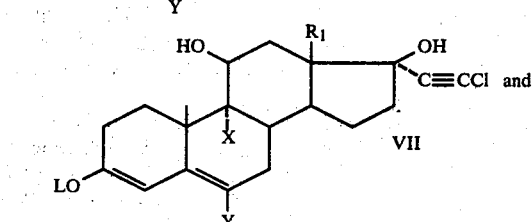

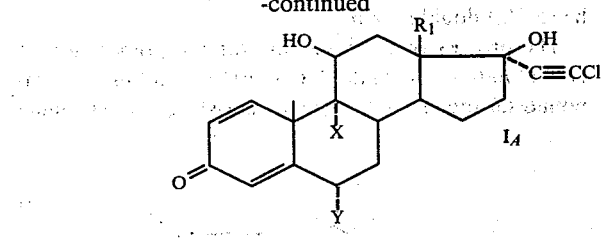

which may be isolated, if desired, and reacting a compound of formula VI or VII with an acid hydrolysis agent to obtain a compound of the formula

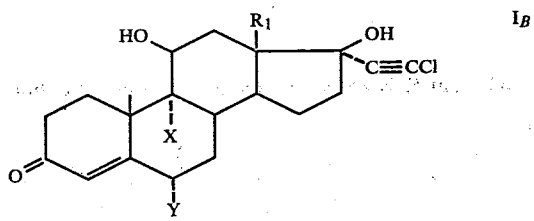

or with an agent capable of freeing the ketone group and creating a $\Delta^{4,6}$-double bond system to obtain a compound of the formula

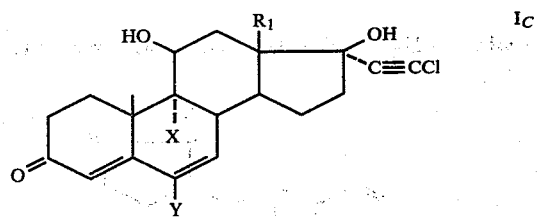

or with an agent capable of freeing the ketone group and creating a $\Delta^{1,4,6}$ double bond system to obtain a compound of the formula

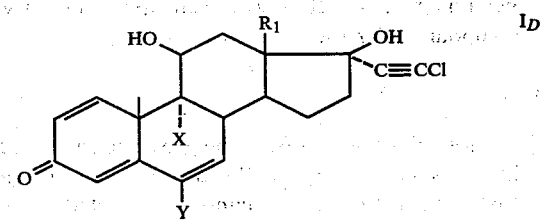

and optionally reacting a compound of formulae $I_A$, $I_B$, $I_C$ or $I_D$ with an esterification agent capable of introducing an acyl group of an organic carboxylic acid of 1 to 18 carbon atoms to obtain the corresponding ester of formula I.

When K is a ketal, K is preferably acyclic alkylketal of 2 to 4 carbon atoms such as ethyleneketal or propyleneketal or a dialkylketal such as dimethylketal or diethylketal. When K is a ketone blocked in the form of a oxime, K is preferably —NOH or —NOAlk where Alk is alkyl of 1 to 4 carbon atoms. L is preferably methyl, ethyl or n-propyl and Hal is preferably bromine.

The chloroethynylation agent of formula V is preferably formed in situ by transforming cis-dichloroethylene or trichloroethylene to lithium chloroacetylene with a base such as lithium diisopropylamide or methyllithium and especially butyllithium. Examples of acid hydrolysis agents are hydrochloric acid, sulfuric acid, acetic acid, citric acid or p-toluene sulfonic acid.

The agent capable of freeing the ketone group and creating the $\Delta^{4,6}$-double bond system is preferably a p-benzoquinone derivative such as 2,3-dichloro-5,6-dicyano-benzoquinone or chloranil and the reaction is preferably effected in aqueous acetone but the $\Delta^{4,6}$-double bond system may be obtained by biochemical means such as with Arthrobacter Simplex. The agent capable of freeing the ketone group and creating the $\Delta^{1,4,6}$-double bond system is preferably a p-benzoquinone derivative such as chloranil or 2,3-dichloro-5,6-dicyano-benzoquinone and the reaction is effected in benzene.

The preferred esterification agent has the formula

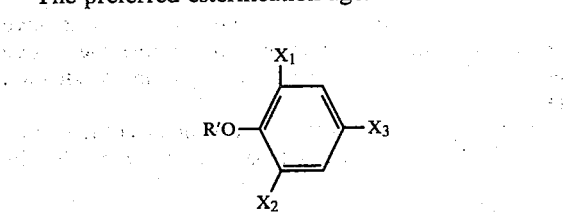

wherein R' is an acyl of an organic carboxylic acid and $X_1$, $X_2$ and $X_3$ are individually either hydrogen or nitro with at least one of the X's being nitro. In a preferred mode of the process, the esterification agent is

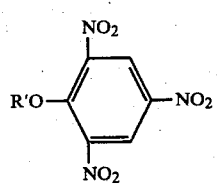

and is formed in situ by reacting picric acid with a compound of the formula R'-Hal and Hal is preferably chlorine. The esterification agent may also be an organic carboxylic acid or a functional derivative thereof such as the acid halide or anhydride and the reaction is effected by known methods.

The anti-inflammatory compositions of the invention are comprised of an anti-inflammatorily effective amount of at least one compound of formula I and an inert pharmaceutical carrier or excipient. The compositions may be in the form of tablets, coated tablets, cachets, capsules, granules, emulsions, syrups, suppositories, injectable solutions or suspensions, pomades, creams, gels and aerosol preparations.

Examples of suitable excipients are talc, starch, lactose, magnesium stearate, aqueous or non-aqueous vehicles, fatty bodies of animal or vegetable origin, paraffinic derivatives, glycols, diverse wetting agents, dispersants or emulsifiers or preservatives.

The compositions are useful for treatment of inflammatory reactions such as edemas, dermatosis, pruritsis, diverse forms of eczema, solar erythemea, polyarthritsis, arthrosis or lombalgia.

Particularly preferred are the compositions containing 21-chloro-$\Delta^{1,4,6}$-pregnatriene-20-yn-11$\beta$,17$\beta$-diol-3-one and 6-methyl-21-chloro-$\Delta^{1,4,6}$-pregnatriene-20-yn-11$\beta$,17$\beta$-diol-3-one.

The novel method of the invention for the treatment of inflammation in warm-blooded animals, including humans, comprises administering an anti-inflammatorily effective amount of at least one compound of formula I.

The compounds may be administered orally, rectally, parenterally or topically to skin or mucous. The daily effective dose is depending on the affection being treated, and the subject being concerned. It can be between 2 mg and 20 mg daily by oral route with the product of example 2, or 1 to 4 daily applications with a pomade containing from 0,1 to 5% of the product of example 3.

The starting compounds of formulae II, III and IV are generally known and can be prepared by known procedures such as described in French Pat. Nos. 1,359,611 and 1,222,424 and U.S. Pat. Nos. 3,010,957 and 3,072,684.

In the following examples there are described several preferred embodiments to illustrate the invention. However, it should be understood that the invention is not intended to be limited to the specific embodiments.

EXAMPLE 1

21-chloro-$\Delta^{1,4,6}$-pregnatriene-20-yn-11$\beta$,17$\beta$-diol-3-one

STEP A: 3-ethoxy-$\Delta^{3,5}$-androstadiene-11$\beta$-ol-17-one

A mixture of 43 g of $\Delta^4$-androstene-11$\beta$-ol-3,17-dione (prepared in U.S. Pat. No. 3,072,684), 215 ml of ethanol and 43 ml of a solution of 0.26 M of ethyl orthoformate was heated to 50° C. and 5.2 ml of a solution of 0.48 g of p-toluene sulfonic acid in 50 ml of ethanol were added thereto. The mixture was held at 50° C. for 5 minutes and then 8.6 ml of triethylamine were added to the mixture which was then cooled to 20° C. 258 ml of water were added to the mixture and the mixture was held at 0 to 5° C. for one hour and was filtered. The recovered product was washed with a 50-50-0.5 ethanol-water-pyridine mixture to obtain 40.1 g of 3-ethoxy-$\Delta^{3,5}$-androstadiene-11$\beta$-ol-17-one which was used as is for the next step.

STEP B: 21-chloro-$\Delta^{1,4,6}$-pregnatriene-20-yn-11$\beta$,17$\beta$-diol-3-one 48 ml of anhydrous tetrahydrofuran were added with stirring at 0° C. under an inert atmosphere to 60.5 ml of n-butyllithium in hexane and then 13.2 ml of diisopropylamine were added dropwise to the mixture. The mixture was cooled to $-70°$ C. and 3.8 ml of cis 1,2-dichloro-ethylene were added thereto over one minute. The temperature was allowed to return to room temperature and then a solution of 3 g of the product of Step A in 15 ml of anhydrous tetrahydrofuran was added to the mixture. The mixture was stirred for 2¾ hours, was washed with cold ammonium chloride solution and was extracted with ether. The ether extracts were washed with sodium bicarbonate solution, dried over sodium sulfate and evaporated to dryness to obtain 4.6 g of a reddish-maroon foam.

A solution of 7.5 g of 2,3-dichloro-5,6-dicyanobenzoquinone in 215 ml of anhydrous benzene was added to a solution of 4.35 g of the foam product in 55 ml of anhydrous benzene and the mixture was stirred for 30 minutes. Then, 30 ml of acetone were added to the mixture which was then poured into 150 ml of aqueous saturated sodium bicarbonate solution. The mixture was extracted with benzene and the organic phase was washed twice with 0.5 N sodium thiosulfate solution, once with sodium bicarbonate solution, once with distilled water, dried over sodium sulfate and evaporated to dryness. The residue was chromatographed over silica gel and was eluted with an 8-2 chloroform-acetone mixture to obtain 1.155 g of a foam. The latter was crystallized from isopropyl ether and then from an isopropyl ether-methylene chloride-methanol mixture to obtain 0.922 g of 21-chloro-$\Delta^{1,4,6}$-pregnatriene-20-yn-11$\beta$,17$\beta$-diol-3-one in the form of cream colored crystals melting at 250° C.

Analysis: $C_{21}H_{23}ClO_3$; molecular weight=358.87, Calculated: %C 70.28 %H 6.46 %Cl 9.88. Found: 70.1 6.3 10.0.

EXAMPLE 2

6-methyl-21-chloro-$\Delta^{1,4,6}$-pregnatriene-20-yn-11$\beta$,17$\beta$-diol-3-one STEP A: 3-ethoxy-6-methyl-$\Delta^{3,5}$-androstadiene-11$\beta$-ol-17-one A suspension of 1.80 g of 6$\alpha$-methyl-$\Delta^4$-androstene-11$\beta$-ol-3,17-dione in 10 ml of ethanol and 2 ml of triethoxymethane was stirred under nitrogen at 50° C. and 0.25 ml of a solution of 480 mg of p-toluene sulfonic acid in 50 ml of ethanol was added thereto. The mixture was stirred for 5 minutes and then 0.4 ml of triethylamine was added thereto. The mixture was cooled in an ice bath while water was added dropwise and the mixture was vacuum filtered. The recovered product was washed with a 7-3 ethanol-water mixture and dried to obtain 1.66 g of 3-ethoxy-6-methyl-$\Delta^{3,5}$-androstadiene-11$\beta$-ol-17-one with an Rf=0.55 (1-1 benzene-ethylacetate mixture).

STEP B: 6-methyl-21-chloro-$\Delta^{1,4,6}$-pregnatriene-20-yn-11$\beta$,17$\beta$-diol-3-one 45 ml of anhydrous tetrahydrofuran were added with stirring under an inert atmosphere of 0° C. to 45 ml of n-butyllithium in hexane and then 7.1 ml of diisopropylamine were added thereto dropwise. The mixture was cooled to $-75°$ C. and 1.89 ml of cis 1,2-dichloroethylene were added thereto dropwise while keeping the temperature less than $-40°$ C. The temperature was allowed to rise to room temperature and the mixture was then stirred for one hour and was then allowed to stand for precipitation to occur. 2.5 g of the product of Step A were added to the mixture which was then stirred for 2 hours. The resulting brown solution was poured into aqueous ammonium chloride solution and the mixture was extracted with ethanol. The organic phase was washed with aqueous sodium bicarbonate solution, dried over sodium sulfate and evaporated to dryness under reduced pressure. The residue was pressure chromatographed over silica gel and was eluted with a 7-3 benzene-ethyl acetate mixture to obtain 2.9 g of pure product.

The said 2.9 g were dissolved in 80 ml of anhydrous benzene and a solution of 5 g of 2,3-dichloro-5,6-dicyanobenzoquinone in 120 ml of anhydrous benzene was added thereto. The mixture was stirred at room temperature for 30 minutes and was poured into aqueous sodium bicarbonate solution. The mixture was extracted with ether and the organic phase was washed with aqueous 0.5 N sodium thiosulfate solution and with aqueous sodium bicarbonate solution, was dried over sodium sulfate and evaporated to dryness under reduced pressure. The residue was pressure chromatographed over silica gel and was eluted with a 1-1 benzene-ethyl acetate mixture. The product was crystallized from methanol to obtain 1.71 g of 6-methyl-21-chloro-$\Delta^{1,4,6}$-pregnatriene-20-yn-11$\beta$,17$\beta$-diol-3-one solvated with 4% methanol.

Analysis: $C_{22}H_{25}O_3Cl$ 0.5 $CH_3OH$; molecular weight=372.88, Calculated: %C 69.48 %H 6.99 %Cl 9.12. Found: 69.4 6.8 9.1.

EXAMPLE 3

21-chloro-$\Delta^{1,4}$-pregnadiene-20-yn-11β,17β-diol-3-one 70 ml of anhydrous tetrahydrofuran and then 12.9 ml of diisopropylamine were added at 0° C. with stirring under an inert atmosphere to 70 ml of a solution of 1.3 M of n-butyllithium in hexane and after cooling the mixture to −75° C., 1.89 ml of cis-1,2-dichloroethylene were added thereto dropwise while keeping the temperature below −40° C. The temperature was allowed to rise to room temperature and the mixture was stirred for one hour and was then allowed to stand. 5 g of $\Delta^{1,4}$-pregnadiene-11β-ol-3,17-dione (described in U.S. Pat. No. 3,010,957) were added to the mixture which was then washed with aqueous ammonium chloride solution. The mixture was extracted with ether and the organic phase was washed with aqueous sodium bicarbonate solution, dried over sodium sulfate and evaporated to dryness under reduced pressure. The residue was pressure chromatographed over silica gel and was eluted with a 1-1 benzene-ethyl acetate mixture. The solution was treated with activated carbon and the product was crystallized twice from a methylene chloride-isopropyl ether mixture to obtain 21-chloro-$\Delta^{1,4}$-pregnadiene-20-yn-11β,17β-diol-3-one in the form of cream colored crystals melting at 212° C.

Analysis: $C_{21}H_{25}O_3Cl$; molecular weight=360.87, Calculated: %C 69.89 %H 6.98 %Cl 9.83. Found: 70.1 7.3 10.2.

EXAMPLE 4

A pomade for topical application was prepared containing 3 g of 21-chloro-$\Delta^{1,4}$-pregnadiene-20-yn-11β,17β-diol-3-one and sufficient excipient of lanolin and vaseline for a total weight of 100 g.

Tablets were prepared containing 5 mg of 6-methyl-21-chloro-$\Delta^{1,4,6}$-pregnatriene-20-yn-11β,17β-diol-3-one and sufficient excipient of lactose, starch, talc and magnesium stearate for a final weight of 100 mg.

PHARMACOLOGICAL STUDY

A. Dermic Activity

The dermic activity of the products of the invention was determined by the croton edema test inspired by Tonelli et al [Endocrinology, Vol. 77 (1965), p. 625]. An edema was produced in mice by the application of croton oil to one ear and in the first group of mice, the croton oil solution was applied to the right ear. The mice in the second group received an application of croton oil solution containing the test product. Nothing was applied to the left ear of either group of mice. After 6 hours, the ears were cut off and weighed and the difference in weight between the left and right ears was the degree of inflammation. The results expressed as $CA_{50}$, the concentration of test product which diminished the edema provoked by croton oil by 50% as compared to the controls, are reported in Table I.

TABLE I

| Compound of Example | $CA_{50}$ in mg/ml |
|---|---|
| 1 | 1.0 |
| 2 | 1.0 |
| 3 | 0.4 |

The results of Table 1 show that the compounds have a local activity with the product of Example 3 having a remarkable local activity.

B. Oral Anti-inflammatory Activity

The anti-inflammatory activity was determined by the granuloma test modified by Meier et al [Experientia, Vol. 6, (1950), p. 469] in which the test products were used in the form of aqueous dispersions containing 0.25% of carboxymethylcellulose and 0.20% of Polysorbate 80. Conventional female Wistar rats weighing 100 to 110 g received an implantation of 2 cotton pellets weighing 10 mg each in the skin of the thorax. The test compounds were orally administered twice a day for 2 days and 16 hours after the last administration or the 3rd day, the rats were killed. The pellets together with the granuloma tissue formed were weighed in the fresh state and then after 18 hours at 60° C. The granuloma weight was obtained by subtracting the initial cotton weight and the results, expressed as the $DA_{50}$ dose which inhibited the granuloma by 50%, are reported in Table II.

TABLE II

| Compound of Example | $DA_{50}$ in mg/kg |
|---|---|
| 1 | 9 |
| 2 | 3.5 |
| 3 | 3 |

The results of Table II show that the tested products have a good anti-inflammatory activity.

Various modifications of the products and processes of the invention may be made without departing from the spirit or scope thereof and it should be understood that the invention is intended to be limited only as defined in the appended claims.

What we claim is:

1. A 21-chloro-20-acetylenic steroid of the formula

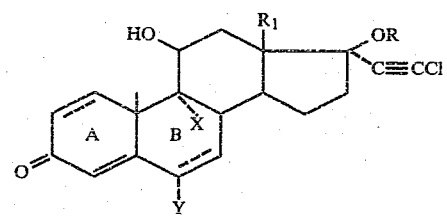

wherein $R_1$ is alkyl of 1 to 3 carbon atoms, R is selected from the group consisting of hydrogen and acyl of an organic carboxylic acid of 1 to 18 carbon atoms, X is selected from the group consisting of hydrogen, chlorine, bromine and fluorine, Y is selected from the group consisting of hydrogen, fluorine and methyl and the dotted lines in the A and B rings are one or two optional double bonds in the 1(2) and 6(7) positions with the proviso that Y is not hydrogen when $R_1$ is methyl, X is hydrogen, the A ring is saturated in the 1(2) position and the B ring is saturated.

2. A compound of claim 1 wherein $R_1$ is methyl.
3. A compound of claim 1 wherein X is hydrogen.
4. A compound of claim 1 wherein the A ring has a 1(2) double bond.
5. A compound of claim 1 wherein R is hydrogen.
6. A compound of claim 1 which is 21-chloro-$\Delta^{1,4,6}$-pregnatriene-20-yn-11β,17β-diol-3-one.

7. A compound of claim 1 which is 6-methyl-21-chloro-$\Delta^{1,4,6}$-pregnatriene-20-yn-11$\beta$,17$\beta$-diol-3-one.

8. A compound of claim 1 which is 21-chloro-$\Delta^{1,4}$-pregnadiene-20-yn-11$\beta$,17$\beta$-diol-3-one.

9. An anti-inflammatory composition comprising an anti-inflammatorily effective amount of at least one compound of claim 1 and an inert pharmaceutical carrier.

10. A composition of claim 9 wherein $R_1$ is methyl.

11. A composition of claim 9 wherein X is hydrogen.

12. A composition of claim 9 wherein the A ring has a 1(2) double bond.

13. A composition of claim 9 wherein R is hydrogen.

14. A composition of claim 9 which is 21-chloro-$\Delta^{1,4,6}$-pregnatriene-20-yn-11$\beta$,17$\beta$-diol-3-one.

15. A composition of claim 9 which is 6-methyl-21-chloro-$\Delta^{1,4,6}$-pregnatriene-20-yn-11$\beta$,17$\beta$-diol-3-one.

16. A composition of claim 9 which is 21-chloro-$\Delta^{1,4}$-pregnadiene-20-yn-11$\beta$,17$\beta$-diol-3-one.

17. A method of treating inflammation in warm-blooded animals comprising administering to warm-blooded animals an anti-inflammatorily effective amount of at least one compound of claim 1.

18. A method of claim 17 wherein $R_1$ is methyl.

19. A method of claim 17 wherein X is hydrogen.

20. A method of claim 17 wherein A ring has a 1(2) double bond.

21. A method of claim 17 wherein R is hydrogen.

22. A method of claim 17 which is 21-chloro-$\Delta^{1,4,6}$-pregnatriene-20-yn-11$\beta$,17$\beta$-diol-3-one.

23. A method of claim 17 which is 6-methyl-21-chloro-$\Delta^{1,4,6}$-pregnatriene-20-yn-11$\beta$,17$\beta$-diol-3-one.

24. A method of claim 17 which is 21-chloro-$\Delta^{1,4}$-pregnadiene-20-yn-11$\beta$,17$\beta$-diol-3-one.

* * * * *